United States Patent [19]

Spiegelman et al.

[11] Patent Number: 5,137,734

[45] Date of Patent: Aug. 11, 1992

[54] ANGIOGENIC MONOGLYCERIDES

[75] Inventors: Bruce M. Spiegelman; John J. Castellot, Jr., both of Newton; Deborah E. Dobson, Jamaica Plains, all of Mass.

[73] Assignees: Dana Farber Cancer Institute, Boston; President and Fellows of Harvard College, Cambridge, both of Mass.

[21] Appl. No.: 327,314

[22] Filed: Mar. 22, 1989

[51] Int. Cl.$^5$ .............................. A61K 31/19
[52] U.S. Cl. ................... 424/574; 514/557; 514/549; 514/552; 514/546
[58] Field of Search .................. 424/574; 514/557

[56] References Cited

U.S. PATENT DOCUMENTS

| | | | |
|---|---|---|---|
| 3,952,107 | 4/1976 | Shibata | 514/547 |
| 4,503,038 | 3/1985 | Banda et al. | 424/537 |
| 4,698,301 | 10/1987 | Weiss et al. | 435/41 |
| 4,735,967 | 4/1988 | Neesby | 514/557 |
| 4,822,821 | 4/1989 | Perrine | 514/557 |
| 4,879,312 | 11/1989 | Kamarei et al. | 514/560 |
| 4,888,324 | 12/1989 | Catsimpoolas et al. | 514/25 |

FOREIGN PATENT DOCUMENTS

| | | |
|---|---|---|
| 0314105 | 3/1989 | European Pat. Off. |
| 8703486 | 6/1987 | PCT Int'l Appl. |
| 8703804 | 7/1987 | PCT Int'l Appl. |

OTHER PUBLICATIONS

West et al., (1985) Science 228:1324–1328.
Goldsmith et al., (1984) JAMA 252(15)2034–2036.
Castellot et al., (1980) Proc. Natl. Acad. Sci. USA 77(10):6007–6011.
Kull et al., (1987) Science 236:843–835.
Castellot et al., (1982) Proc. Natl. Acad. Sci. 79:4997–5601.
Castellot et al., (1986) Journal of Cellular Physiology 127:323–329.

*Primary Examiner*—Douglas W. Robinson
*Assistant Examiner*—Jean C. Witz
*Attorney, Agent, or Firm*—Morrison & Foerster

[57] ABSTRACT

Monoglycerides of the formula:

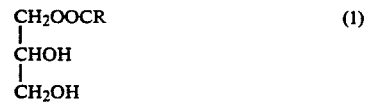

wherein R is an aliphatic hydrocarbyl moiety of 2–10 C, straight chain or branched, saturated or unsaturated, and optionally substituted with one or more substituents which do not interfere with angiogenic activity are capable of stimulating angiogenesis *in vivo*. These compounds, and their pharmaceutical compositions, are useful in wound healing and other therapeutic applications where stimulation of vascularization is beneficial. Antibodies to these materials have also been prepared and are useful in diagnosis and therapy.

7 Claims, 6 Drawing Sheets

ANGIOGENIC MONOGLYCERIDES

This invention was supported under NIH Grant ROL-HL30290 and the United States Government has certain rights to this invention.

TECHNICAL FIELD

The invention is related to therapeutic compositions for stimulating vascularization in warm-blooded animals. In particular, the invention concerns monoglycerides which are effective in stimulating angiogenesis.

BACKGROUND ART

"Angiogenesis" refers to the growth of new blood vessels, or "neovascularization", and involves the growth of capillaries composed of endothelial cells. Angiogenesis is an integral part of many important biological processes, including cancer cell proliferation, inflammation, wound healing, the menstrual cycle, and fetal development. New blood vessel formation is required for the development of any new tissue, whether normal or pathological, and thus represents a potential control point in regulating many disease states, as well as a therapeutic opportunity for encouragement of the growth of normal tissue.

One paradigm for this process is encountered early in embryonic development when primordial cells form "blood islands," the cells of which give rise to capillaries, which in turn form the larger veins and arteries in the process of vasculogenesis. However, once the vascular system is formed, usually by the end of the first third of embryonic development, new capillaries, including those which arise later in the embryo and in the adult, are derived from existing vessels. It is this angiogenesis or neovascularization phenomenon to which the invention is applied.

The complete process of angiogenesis is not entirely understood, but it is known to involve the endothelial cells of the capillaries in the following ways:

1) The attachment between the endothelial cells and the surrounding extracellular matrix is altered, presumably mediated by proteases and glycosidases which may be produced at enhanced levels during this process;

2) There is a "chemotactic" process of migration of the endothelial cells toward the tissue to be vascularized; and 3) There is a "mitogenesis" process—i.e., proliferation of the endothelial cells to provide additional cells for the new vessels.

Each of these activities involved in angiogenesis: proteolysis, chemotaxis, and mitogenesis, can be measured independently in in vitro endothelial cell cultures. In addition, the overall angiogenic stimulation of a test substance can be measured in model systems such as the chick chorioallantoic system (which measures angiogenic activity in an embryonic system), and in the rabbit corneal pocket assay and in hamster cheek pouch assay (which measure angiogenic activity in more mature systems).

A number of factors are known to stimulate angiogenesis. Many of these are peptide factors, and the most notable among these are the fibroblast growth factors, both acidic and basic which can be isolated from a variety of tissues including brain, pituitary, and cartilage. A discussion of various peptide factors involved in angiogenesis, including acidic and basic FGF is found in, for example, PCT application WO87/01728 published Mar. 26, 1987 and incorporated herein by reference. Both isolated and recombinant forms of many of these proteins are now available.

Other factors which are known to show angiogenic-stimulating activity, but which are not proteins, include prostaglandins E1 and E2 (Ben-Ezra, D., et al., *Am J Opthamol* (1978) 86:445–461) fragments of hyaluronic acid (West, D. C., et al., *Science* (1985) 228:1324–1326) and nicctinamide (Kull, F. C., et al., *Science* (1987) 236:843–845).

A series of papers published by groups from Boston University and Angio Medical Corporation led by N. Catsimpoolas, describe the isolation of a lipid angiogenic factor from omentum. A preliminary communication appeared in *JAMA* (1984) 252:2034–2036. There are also a number of patent publications from this group, including PCT applications WO87/03804, WO87/03811 and WO87/03812, all published Jul. 2, 1987; WO87/03486, published Jun. 18, 1987; WO87/06136, published Oct. 22, 1987; and U.S. Pat. No. 4,699,788, issued Oct. 13, 1987. These applications describe and claim use of compositions of omental lipids or fractions for skin care and cosmetics or for angiogenesis and epithelialization.

In addition, conditioned media from 3T3 adipocytes, but not from undifferentiated 3T3 cells, has been shown to stimulate angiogenesis related processes in endothelial cells (Castellot, J. J., Jr., et al., *Proc Natl Acad Sci USA* (1980) 77:6007–6001). This paper described mitogenic activity for endothelial cells in vitro exhibited by the 3T3 adipocyte culture medium which was insensitive to proteasee, not inactivated by heat, and dialyzable.

Further work by this same group, which includes the inventors herein, showed that these conditioned media (but not the medium conditioned by preadipocytes) could stimulate angiogenesis in the chicken chorioallantoic membrane (CAM) model, and that this stimulation was potentiated by heparin. (Castellot, J. J., Jr., et al., *Proc Natl Acad Sci USA* (1982) 79:5597–5601). The conditioned medium was also shown to effect chemotaxis and motility in the Boyden chamber assay described by Zigmond, S., et al., *J Exp Med* (1973) 137:387–410; Postlethwaite, A. E., et al., *J Exp Med* (1976) 144:1188–1203; and by Grotendorst, G. R., et al., *Proc Natl Acad Sci USA* (1981) 78:369–372, all incorporated herein by reference.

Further characterization of the heparin potentiation of the adipocyte-stimulated angiogenesis was reported by the same group (Castellot, J. J., Jr., et al. (1986) 127:323–329. This work showed that both anticoagulant and nonanticoagulant heparin were capable of potentiation of the activity of the 3T3 adipocyte-conditioned media in the CAM assay.

When the three aspects of angiogenesis separable in vitro were tested, it was found that heparin potentiated the effect of the conditioned media on protease activity (measured as pasminogen activator activity) and motility but did not affect the mitogenic activity of the medium. The effect of heparin on the protease activity depended on the nature of the protease-heparin stimulated tissue plasminogen activator activity, but inhibited urokinase activity.

The present invention provides purified and synthetic factors capable of angiogenesis which are suitable for pharmaceutical formulation and administration. These factors are members of a group of compounds which are low molecular weight monoglycerides.

DISCLOSURE OF THE INVENTION

The angiogenic compounds of the invention are represented by the formula:

$$\begin{array}{l} CH_2OOCR \\ | \\ CHOH \\ | \\ CH_2OH \end{array} \qquad (1)$$

wherein R is a straight or branched chain aliphatic hydrocarbyl of 2°–10° C., which is saturated or unsaturated, and which may be substituted by one or more substituents which do not interfere with the angiogenic activity of the compound. The activity of this group of compounds is synergistic with mitogenic factors, such as fibroblast growth factor.

Accordingly, in one aspect, the invention is directed to pharmaceutical compositions for angiogenesis stimulation, and methods to stimulate angiogenesis which employ the compounds of formula 1 either alone, or in combination with other factors having angiogenesis-promoting activities, such as fibroblast growth factor.

In another aspect, the invention is directed to antisera or individual antibodies immunoreactive with the angiogenic compounds of the invention, to methods to assess the level of angiogenic compounds using these antibodies, and to methods to arrest vascularization by passive immunotherapy.

MODES OF CARRYING OUT THE INVENTION

Preparation and Characterization of Angiogenic Factor from 3T3 Conditioned Medium The conditioned medium of differentiated 3T3 adipocytes is separated into hydrophilic and hydrophobic fractions using any convenient means, but typically using a reverse phase chromatography method. The hydrophilic fraction, as noted above, is capable of stimulating mitogenesis. The lipid soluble material, which is retained on a reverse phase column, is angiogenic but not mitogenic. An illustrative separation of these materials is as follows:

Dishes (100 mm) of 3T3-F442A adipocytes are covered with 5 ml serum-free Dulbecco's modified Eagle's medium for 24 hr. (If desired, in order to characterize the lipid-like angiogenic factor, a small amount of labeled precursor may be introduced during conditioning.) The adipocyte-conditioned medium is then passed over C18 Sep-Pak columns, washed extensively with phosphate buffered saline (PBS) and then eluted with increasing concentrations of aqueous ethanol. The flow-through and the eluate fractions can be assayed using the CAM assay for angiogenesis as described below, for chemotactic activity using Boyden chambers (as described above), and for mitogenesis using bovine aortic endothelial cells (BAEC cells) as described by Castellot, J. J., Jr., et al. Proc Natl Acad Sci USA (1980) 77:6007–6011, cited above and incorporated herein by reference.

Figure 1:
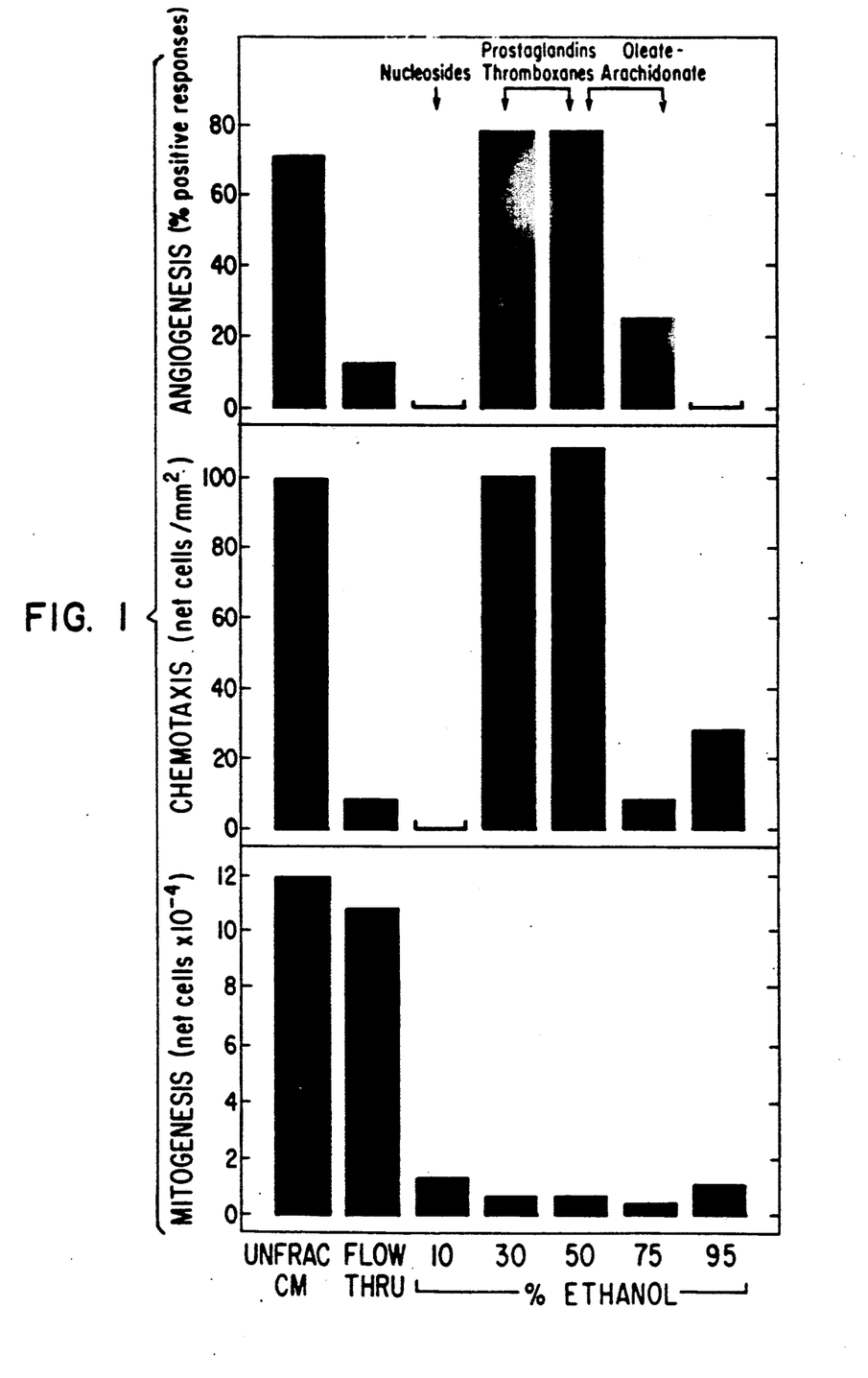
FIG. 1 shows the angiogenesis, chemotaxis, and mitogenesis activity of column fractions from adipocyte-conditioned medium.

FIG. 1 shows the elution pattern of a typical column. In this illustrative example, 20 ml of 3T3 adipocyte-conditioned medium was applied to 2 Sep-Pak C18 columns and fractions were eluted in 2 ml portions with the indicated percentages of aqueous ethanol, evaporated to dryness and resuspended in 2 ml control medium containing 0.2% ethanol for assay.

The top frame of FIG. 1 shows the results of the CAM test for angiogenesis, which is reported as the percentage of positive responses, when at least 40 samples were tested for each fraction. As shown, the angiogenesis activity occurs in the flowthrough, as well as in the eluate fractions representing 30 and 50% ethanol.

The second pattern in the middle frame of FIG. 1 represents the results of chemotaxis assay reported as the net cells/mm$^2$ on each medium test filter minus the number of cells/mm$^2$ on a control medium filter. As shown in this elution pattern the chemotaxis stimulation pattern tracks angiogenesis.

Mitogenesis is reported as the number of cells in the test medium minus the number of cells in control medium, and is shown in the third tier of FIG. 1. The mitogenic activity is confined to the flowthrough volume, and does not appear in the eluate.

The angiogenesis-stimulating fractions in the hydrophobic eluate were further characterized by labeling the cells with 50 uCi 14-C acetate or 3-H arachidonate for 16 hr and subjecting the 30–50% ethanol fractions resulting from C18 chromatography of the media to thin-layer chromatography (TLC) on silica gel thin-layer plates (20×20 cm, 19 channels with preabsorbent zone, J. T. Baker Company). The TLC plates were developed using ethylacetate:2,2,4-trimethylpentane:acetic acid:water (110:50:20:10 by volume) with the results of radioautography shown in FIG. 2.

After radioautography, the thin-layer plate was divided into 8 fractions and eluted with absolute ethanol. For each eluate, 25% was evaporated, resuspended in 0.5 ml control medium (0.5% fetal calf serum in DME) containing 0.2% ethanol and tested for angiogenic activity. Samples were used at a concentration equivalent to that of the starting conditioned medium or were further diluted 1:1 with control medium. Control medium alone yielded 11% positives, and all data are derived from at least 40 samples.

The pattern of angiogenic activity is shown in Table 1 below:

TABLE 1

| | Percentage Positive | |
| Fraction | Neat | 1:1 |
| --- | --- | --- |
| 8 | 0 | — |
| 7 | 0 | — |
| 6 | 22 | — |
| 5 | 88 | 87 |
| 4 | 67 | 38 |
| 3 | 25 | — |
| 2 | 12 | — |
| 1 | 11 | — |

Figure 2:
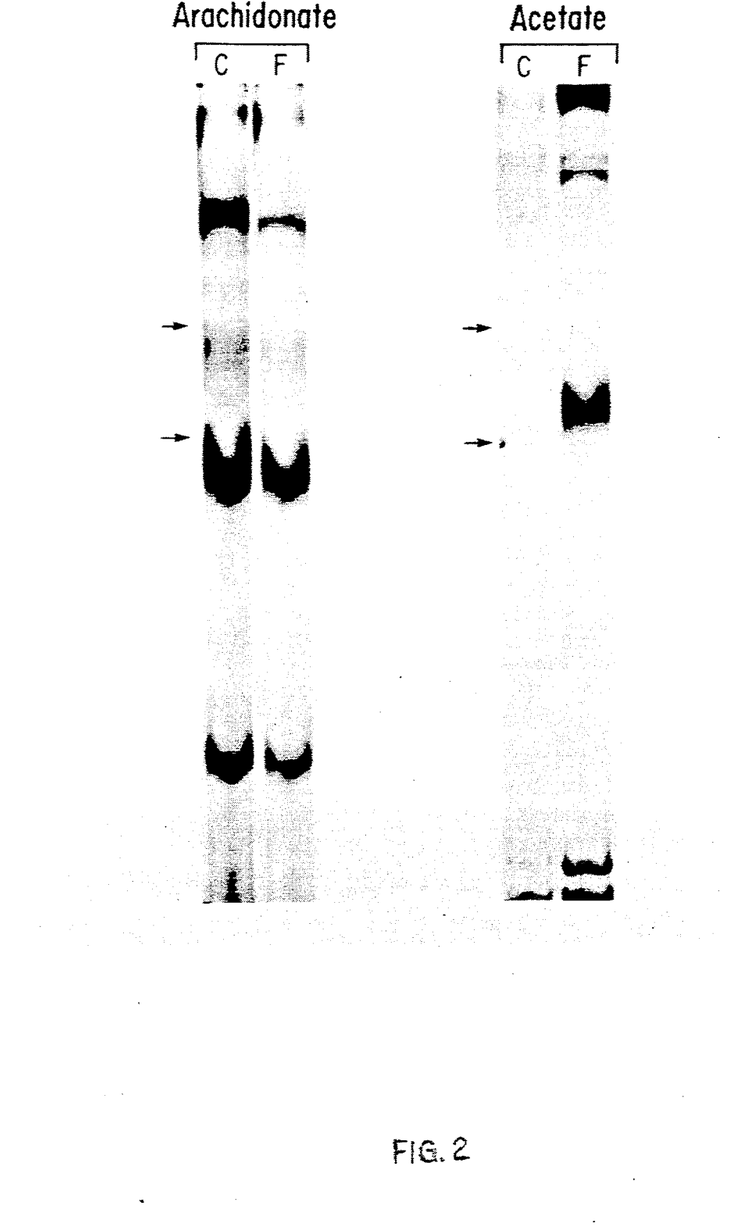
FIG. 2 shows the results of thin-layer chromatography of labeled materials contained in control media or conditioned media when adipocyte cells are labeled with 3-H arachidonate or 14-C acetate.

It is clear that the majority of the activity is in fraction 5, with a little remaining in fraction 4. As shown in FIG. 2, these positions (indicated by the arrows) do not correspond to materials labeled as a result of culturing with labeled arachidonate; however, the cells labeled with 14-C acetate show a labeled band in the position of angiogenic activity which is found only in the conditioned medium, and not in the control. The activity in this band was confirmed by removal of the acetate-labeled band specifically and subjecting the band to the CAM angiogenesis assay. The results were comparable to those exhibited by adipocyte-conditioned medium: the TLC band provided neat gave 85% positive responses in the assay; the adipocyte-conditioned medium provided neat gave 89%; the TLC band diluted 1:49 gave 40% positive responses while similar dilution of the adipocyte-conditioned medium showed 60% positive responses.

Figure 3:
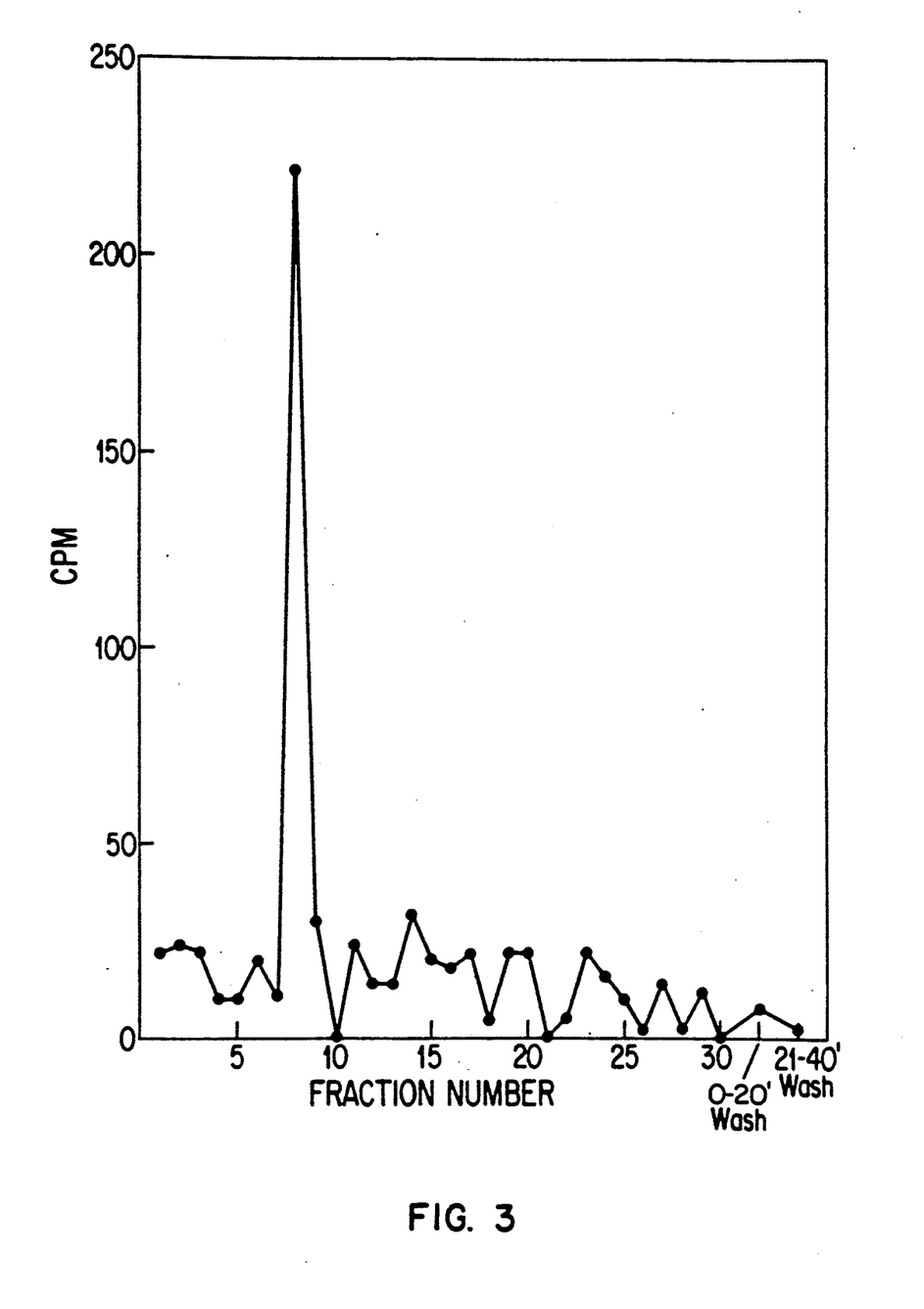
FIG. 3 shows the HPLC profile of 14-C acetate-labeled material purified by TLC from 3T3 adipocytes.
Figure 4A:
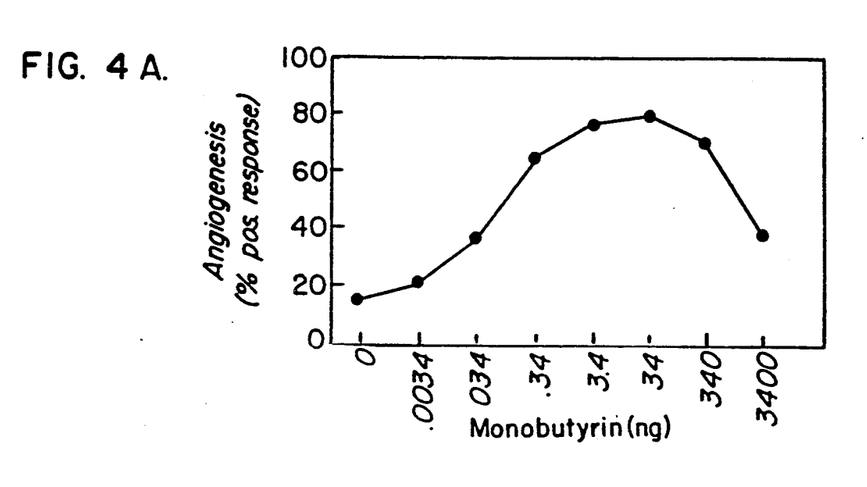
FIGS. 4A–D show the biological activity in angiogenesis, chemotaxis, and protease activity of purified monobutyrin.
Figure 4B:
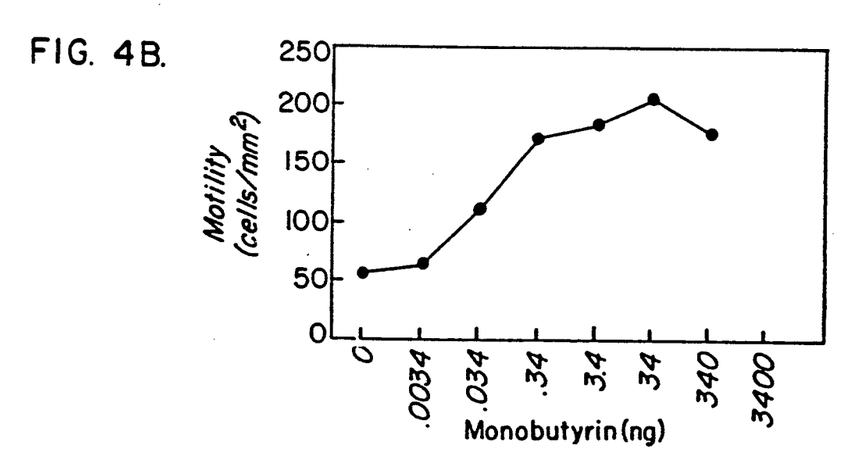
Figure 4C:
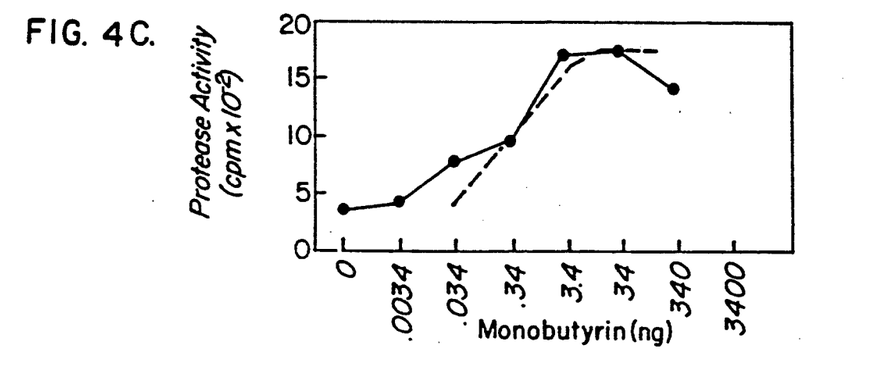
Figure 4D:
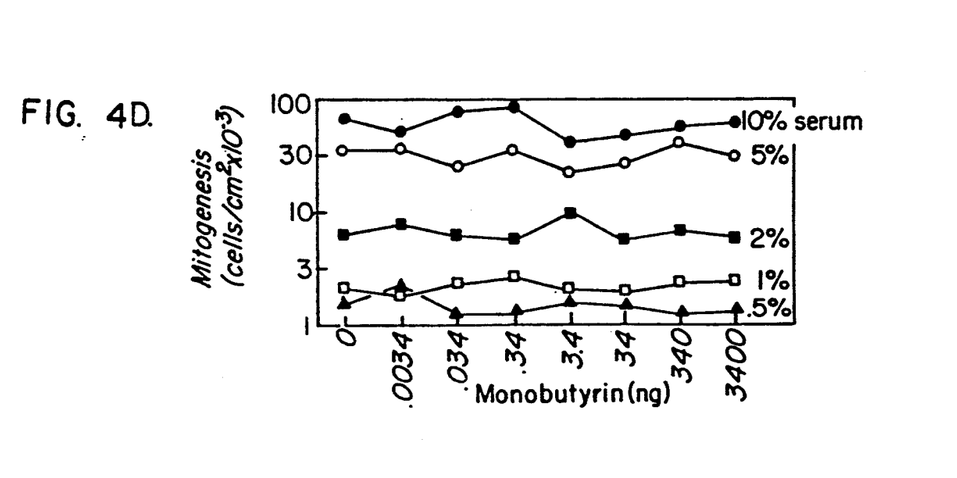

In order to characterize the acetate-labeled material more carefully, 100 ml of the conditioned medium (containing 5 ml 14-C acetate-labeled conditioned medium) was loaded onto a Sep-Pak C18 resin and eluted batchwise with 50% aqueous ethanol. The 50% ethanol sample was then dried, loaded onto a silica gel TLC plate and chromatographed in the organic phase of isooctane:ethylacetate:water (50:10:100). The labeled TLC band was visualized by autoradiography, and a region containing the labeled material was scraped, eluted in absolute ethanol, dried, and resuspended in 0.1 ml water. The suspension was subjected to HPLC on a C18 column (Vydak 218.TP) with Waters Guard-pak Bond-pak using a 0–15% aqueous isopropanol gradient over 30 min (flow rate at 1 ml/min). The column was washed with 60% aqueous isopropanol for 40 min. One ml fractions were collected and a 10 ul sample of each fraction was removed and radioactivity determined by liquid scintillation counting. As shown in FIG. 3, most of the activity appears in fraction 8 and amounts to an overall recovery of 90% of the counts.

The purified fraction in FIG. 3, prepared in a scale-up of the purification described above using 200 ml of the conditioned medium, was subjected to analysis by GC/MS, using electron impact MS, leading to a tentative identification of the peak as comprising mainly monobutyrin—i.e., the compound of formula 1 wherein R is $CH_3CH_2CH_2$—. Synthetic monobutyrin yielded identical analytical data and was tested in the bioassays described in detail below to confirm that the activity contained in the purified material is in fact due to this molecule rather than to an "impurity." The activity pattern for synthetic monobutyrin was virtually identical to that obtained for the purified conditioned medium. These results are shown in FIG. 4.

When purified synthetic monobutyrin was tested in the CAM assay, shown in Panel A of FIG. 4, the results, expressed as percent positive responses from at least 40 samples, showed that 80% positive responses were obtained at about 34 ng/pellet. Panel B shows that a maximal response, expressed in cells/mm$^2$ on polycarbonate filters, was obtained at about 34 ng/ml when purified monobutyrin was tested for chemotactic activity. Panel C shows that plasminogen activator activity, expressed as plasminogen-dependent cpm cleaved from the surface of 24 well cluster dishes coated with 3-H fibrin (31,400 cpm), peaked in the same range; in this case synthetic, but unpurified, monobutyrin was used in the assay. These results lead to estimates of $ED_{50}$ for motility-stimulating activity of $1 \times 10^{-9}$ M. For the unpurified material, an apparent $ED_{50}$ for plasminogen activator-stimulating activity of 5 ng/ml or $3 \times 10^{-8}$ M was obtained.

Further approximate calculations based on the specific activity obtained in the fraction labeled with C14 acetate provides an estimate that under the foregoing growth conditions, adipocyte-conditioned medium contains approximately $6 \times 10^{-8}$ M monobutyrin and the activity obtained for the adipocyte-conditioned medium is thus in good agreement with the activity obtained for monobutyrin.

Monobutyrin at a range of 3.4 pg/ml–3.4 ug/ml was inactive, as was the 30–50% ethanol eluate of the C18 column run on conditioned medium. The synthetic material at a range of 3.4 pg/ml–3.4 ug/ml was unable to stimulate growth of endothelial cells when added to serum in the range of 0.5–10%.

Preparation of the Compounds of the Invention

As set forth in the Background section, a purified hydrophilic fraction from adipocyte-conditioned medium which has mitogenic activity can be obtained. This can be recovered by removing hydrophobic components using conventional means, such as reverse phase affinity chromatography. This purified hydrophilic fraction differs from the lipid-soluble component (monobutyrin) of the adipocyte medium which stimulates angiogenesis and chemotaxis by having also the ability to stimulate cell division and growth—i.e., mitogenesis.

The compounds of formula 1 of the invention, which are angiogenic, but not mitogenic, can be prepared conventionally by esterification of glycerol and purification of the monoesterified product. Isolation of the monoester can be done by any standard means, such as chromatographic separation or fractional distillation. Many of the compounds of formula 1 are commercially available; monobutyrin itself, for example, is available from Eastman Kodak. However, the compounds are readily prepared from the corresponding carboxylic acids or their activated (acyl halide or anhydride, for instance) derivatives and glycerol using standard esterification methods. Purification of the resulting monoesters is accomplished by chromatographic methods, e.g., HPLC, GC, or other standard preparative methods.

Figure 5:
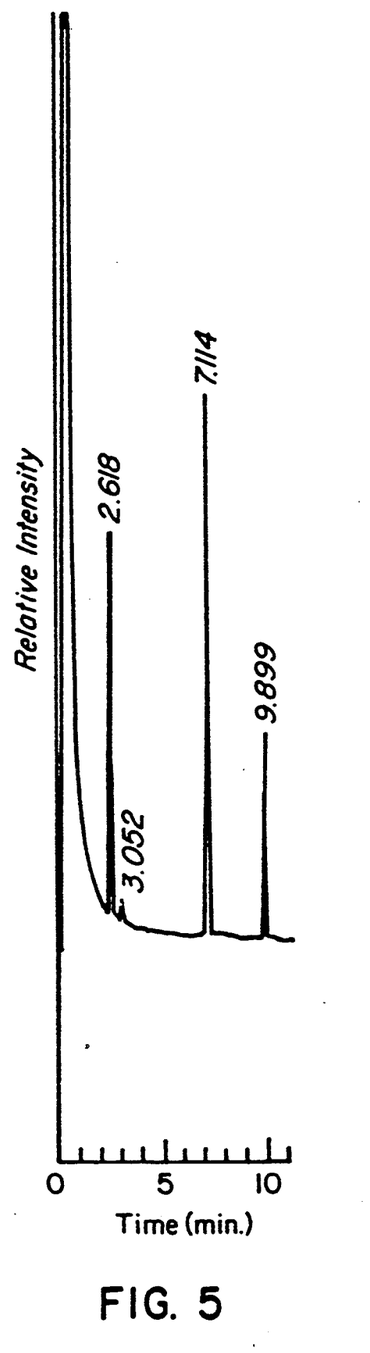
FIG. 5 shows an HPLC trace of vacuum-distilled commercially available practical grade monobutyrin.

For purposes of illustration, a protocol for the purification of commercially available monobutyrin to a purity level of greater than 99% is as follows:

Practical grade monobutyrin having a boiling point of 153° C. is subjected to vacuum distillation at about 3 mm Hg over an oil bath held at 160°–162° C. and the distillate obtained at 137°–138° C. is recovered. This fraction is subjected to chromatography through a 50 cm × 1.5 cm column containing 30 g of silica gel, and eluted by gradient elution with hexane:ethylacetate varying from 90:10–20:80 v/v, collecting 10 ml fractions. In one typical run, fractions 29–33 contained the butyrin. The AGC chromatogram (DB-1 column) run on these fractions is shown in FIG. 5. The first peak eluted from this chromatography, when obtained preparatively, is recrystallized from ether at −70° C. In a typical procedure, this material was shown to be more than 99% pure by GC and TLC, and confirmed by mass spectrometry to be monobutyrin.

Similar purification procedures can be used for commercial or synthetic preparations of this and alternate embodiments of the compound of formula 1.

PREFERRED EMBODIMENTS

In the compounds of formula 1, the group represented by R is a straight chain or branched chain saturated or unsaturated aliphatic hydrocarbyl residue having no substitutions or having one or more substitutions which do not interfere with the angiogenic activity of the compound. Substituents which are preferred are typically those which do not drastically alter the lipophilic character of the compound, and a small rather than large number of substituents, preferably one or two substituents, is preferred. Preferred substituents include halo, in particular chloro, and methoxy.

The compounds of formula 1 contain at least one chiral center and thus can be prepared in optically active form or as racemic mixtures. Unless otherwise specified, the compounds of the invention are racemic, or, in the case of the forms isolated from biological systems, of the naturally occurring stereoisomer. Individual stereoisomers are, however, generally included within the scope of the invention.

The group represented by R may be saturated or unsaturated and, if unsaturated, preferably contains three pi bonds or less, and more preferably two or less. While the embodiments include branched chains, highly branched embodiments are not favored, and straight chain embodiments are preferred. The hydrocarbyl group preferably contains 2-5C, and most preferably 3C; in these embodiments no more than one pi bond is preferred.

The angiogenic activity of the particular embodiment of the compound of formula 1 considered may be verified using the assay described below.

ASSAY METHODS

Angiogenic activity is conveniently measured by the chick chorioallantoic membrane assay using a modification of the shell-less embryo technique described by Dunn et al., *Anat Rec* (1981) 199:33-43. In this procedure, chicken eggs, 60-72 hr after fertilization, are cracked into a plastic wrapped sling, held in a styrofoam drinking cup with a rubber band as described by Castellot, J. J., et al., *J Cell Phys* (1986) 127:323-329. The cup is covered with a sterile plastic top from a 100 mm culture dish and placed in a humidified 37° C. incubator. Nine days after fertilization, 30 ul or 40 ul agarose pellets containing test substances are placed on the chorioallantoic membrane which occupies an area of 30-40 cm² at this stage. (Pellets are prepared by rapidly combining 15 or 20 ul of 6% aqueous low melting point agarose (Sigma Type VII) with an equal volume of test substance at 37° C., thereby avoiding heating of the test substance, and the resulting pellets are kept at 4° C. for several minutes to solidify.)

Observations are made visually, and 5-8 samples can be placed on a single egg. Vascularization is observed visually, and scoring is done in a single-blind fashion on days 2-5 after adding the pellets. Histological sections of positive responses are examined for the presence of inflammatory cells, since inflammation of the membrane could also result in a positive response, and pellets that have clearly elicited an inflammatory response, as evidenced by the translucent pellet becoming white and opaque, are not scored. More than 50% of the embryos ordinarily survive to permit testing.

Results are given as the percentage of pellets of a test substance which show vascularization, of more than 40 pellets typically tested.

The ability of a test substance to elicit a response in vitro corresponding to plasminogen activation, chemotaxis, or mitogenesis can also be tested by standard means. Convenient assay systems to conduct these tests are set forth in Castellot, J. J., Jr., *J Cell Physiol* (1986) 127:323-329, cited above, and incorporated herein by reference.

EFFECT OF ADDED MATERIALS

Combination of the angiogenic compounds of the invention of formula 1 with angiogenic substances which are also mitogenic is beneficial. A number of factors, mostly proteinaceous, which enhance the growth of endothelial cells have been prepared, and a summary and comparison of 13 of these factors is found in Lobb, R., et al., *J Biol Chem* (1986) 261:1924-1928, incorporated herein by reference. Prominent among these factors are platelet-derived growth factor (PDGF), epidermal growth factor (EGF), and the acidic and basic fibroblast growth factors (FGF). These factors, in combination with the compounds of formula 1 of the invention, permit more effective stimulation of, for example, wound healing.

As an illustration, various amounts of monobutyrin and basic FGF, as described in WO87/01728, were combined and assayed in the CAM method set forth above. Control pellets were prepared containing only buffer (0.9% NaCl) and elicited only 9% positive responses. As positive controls, basic FGF at 30 ng/pellet yielded 81% positive responses and higher concentrations of monobutyrin at 340 ng/pellet yielded 92% positives. In the assay, monobutyrin at 34 pg/pellet yielded 24% positive responses; basic FGF at 1 ng/pellet yielded 15% positive responses. An additive effect of mixing 34 pg monobutyrin and 1 ng basic FGF in a pellet would have yielded about 39% positive responses; 72% positives were obtained.

These results show that the monobutyrin and basic FGF behaved in a synergistic manner in this assay.

Preparation of Antisera

The compounds of formula 1 may be rendered immunogenic by conjugation to carrier and used to prepare antiserum using standard procedures. The resulting antibodies are useful in detecting the levels of these materials in subjects who have been administered the compounds for therapeutic purposes, as well as for assessing production of the corresponding native factor, and for antiproliferative therapy, for example in controlling the growth of neoplastic tissue.

Typically, the compound of formula 1 is conjugated to a carrier such as keyhole limpet hemocyanin (KLH), tetanus toxoid, or the relevant serum albumin by means known in the art per se, conveniently employing bifunctional linkers such as those produced by Pierce Chemical Co. The free hydroxyls on the glycerol moiety are convenient functional groups for reaction with linkers which can then be conjugated to carrier.

Immunization is conducted using standard protocols and the antisera obtained and titrated using standard immunoassay procedures with the relevant compound of formula 1 as antigen. If desired, antibody-producing cells of immunized subjects can be immortalized and screened to obtain monoclonal immunoreactive compositions.

Utility and Administration

In one application, the compounds of the invention having angiogenic activity are useful in encouraging wound healing and are generally applied topically to the traumatized tissue. Appropriate substrates are burns, wounds, dermal ulcers, bone fractures, surgical abrasions or incisions such as those of plastic surgery, damaged neurological tissue, peridontal tissue subjected to trauma, grafted skin, and organ transplants.

Systemic or internal conditions which require treatment to encourage vascularization include bone fractures, ligament and tendon repair, tendonitis and bursitis, and tissue repair during ischemia and myocardial infarction. Skin conditions such as burns, bed sores and slow-healing ulcers, as well as superficial wounds and deficient hair growth may benefit from topical administration.

Formulations of the compounds of the invention are prepared using generally known excipients and carriers according to methods known in the art, such as those set forth in *Remington's Pharmaceutical Sciences*, Mack Publishing Co., Easton, Pa. (latest edition).

For topical administration, especially for superficial lesions, standard topical formulations are employed using, for example, $10^{-4}$–1% solutions of the compounds of the invention, with or without added growth preparations would be applied daily or 2-3 times per week to the affected area. The concentration of the solution or other formulation depends on the severity of the wound and the nature of the subject. Formulations can be in a variety of known forms such as ointments, salves, gels, sprays, creams and lotions. In most protocols, the dose is lowered with time to lessen likelihood of scarring.

For bone and tissue repair, local and depot administration is preferred, or administration by subcutaneous or localized implant. Slow release forms can be included in polymers such as Hydron (Langer, R., et al., *Nature* (1976) 263:797-799) or Elvax 40P (DuPont) (Murray, J. B., et al., *In Vitro* (1983) 19:743-747). Other sustained release systems have been suggested by Hsieh, D. S. T., et al., *J Pharm Sci* (1983) 72:17-22.

As to dosage levels, in general, topical, systemic and implanted formulations are designed to achieve a constant local concentration of about 100 times the serum level of the counterpart to the compound of formula 1 or about 10 times the tissue concentration, as described by Buckley et al., *Proc Natl Acad Sci USA* (1985) 82:7340-7344. As the concentration of the factors of formula 1 appears to be quite low, typically, administration of sufficient material to obtain a release of about 10-1000 ng of the compound of formula 1/hr locally is approximately correct.

It should be noted that as these materials are often used in connection with surgery, it may be helpful to imbed them in polymers used as surgical staples or sutures such as polylactic and glycocholic copolymers.

In all cases, but in particular in systemic or implanted local administration, the compounds of the invention can be administered in the form of the corresponding prodrug and converted to the compound of formula 1 in situ. For example, the diglyceride may be used wherein the acyl group esterified to the 2-position of the glycerol is hydrolyzed to generate the compound of formula 1.

The antibody preparations immunoreactive with the compounds of formula 1 of the invention may also be formulated into therapeutic dosages for systemic or local administration using standard administration procedures to control the growth of vascularization in harmful tissues, such as neoplasms or ischemic brain and heart tissue.

ILLUSTRATIVE FORMULATIONS

The following are illustrative of useful formulations in which a compound of formula 1 (or mixtures thereof) is active ingredient. For purposes of example, the active ingredient is set forth as monobutyrin in A and B, and as monocaprylin in C. Other compounds of formula 1 could, of course, be substituted, or a prodrug form could be used.

FORMULATION A

A monobutyrin cream is prepared from the following:

| Ingredient | Amount |
| --- | --- |
| Monobutyrin | 0.1 g |
| Polysorbate-60 | 8.0 g |
| Cetyl Alcohol | 10.0 g |
| Myristyl Stearate | 5.0 g |
| Isopropyl Palmitate | 10.0 g |
| Methyl Paraben | 0.2 g |
| Water q.s. | 100.0 g |

The cetyl alcohol, myristyl stearate, isopropyl palmitate and polysorbate 60 are heated to about 90° C. and melted to obtain an "oil phase".

Most of the required water is heated to 70° C. Methyl paraben is added to the water and stirred until dissolved. Monobutyrin is then added and stirred until dissolved. The resulting aqueous phase is added to the oil phase while both phases are still hot (approximately 60° C.) and stirred and homogenized or worked in colloid mill if necessary. Water is added to make up to 100 g and the mixture is stirred gently until the resulting cream cools.

FORMULATION B

A monobutyrin gel composition is prepared from the following:

| Ingredient | Amount |
| --- | --- |
| Monobutyrin | 0.1 g |
| Hydroxyethylcellulose 250H | 2.0 g |
| Glycerine | 15.0 g |
| Chlorhexidine gluconate | 0.25 g |
| Water q.s. | 100.0 g |

Chlorhexidine gluconate, monobutyrin and glycerine are added to majority of the water and stirred well until complete dissolution occurs. Hydroxyethylcellulose is gradually added and stirred vigorously until all the gelling agents are completely dissolved. Water is then added to 100 g.

FORMULATION C

An ointment product is prepared as follows:

| Ingredient | Amount |
| --- | --- |
| Monocaprylin | 0.1 g |
| Polyethylene | 0.5 g |

| Ingredient | Amount |
| --- | --- |
| Heavy Mineral Oil | 95.0 g |

The monocaprylin is dissolved in heavy mineral oil and heated to 130° C. The polyethylene is added, and the mixture stirred to dissolve. The mineral oil solution is shock cooled and the gel scraped from the cooling drum.

We claim:

1. A method to stimulate angiogenesis in a warm blooded animal, which method comprises administering to a subject in need of such treatment, an amount of a an angiogenic monoglyceride of the formula:

(1)

wherein R is a straight chain or branched chain aliphatic hydrocarbyl substituent of 2-10 C which is saturated or unsaturated, and which is unsubstituted or is substituted with one or more substituents selected from the group consisting of halo substituents and methoxy substituent, which amount is effective to stimulate angiogenesis in said subject.

2. The method of claim 1 wherein R is an unsubstituted straight chain, saturated, hydrocarbyl.

3. The method of claim 2 wherein the compound of formula 1 is monobutyrin.

4. The method of claim 1 wherein the subject requires angiogenesis for wound healing.

5. The method of claim 4 wherein said treatment is by topical administration.

6. The method of claim 1 which further includes administration of an effective amount of a mitogenic factor.

7. The method of claim 6 wherein the factor is basic Fibroblast Growth Factor.

* * * * *